United States Patent
Srivastava et al.

(10) Patent No.: US 9,335,327 B2
(45) Date of Patent: May 10, 2016

(54) ISOLATION AND DETECTION OF CANCER CELLS

(75) Inventors: Shiv K. Srivastava, Potomac, MD (US); Gyorgy Petrovics, Bethesda, MD (US); Shyh-Han Tan, Kensington, MD (US); Kristen Nickens, Clinton, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 14/237,747

(22) PCT Filed: Aug. 8, 2012

(86) PCT No.: PCT/US2012/049997
§ 371 (c)(1),
(2), (4) Date: Feb. 7, 2014

(87) PCT Pub. No.: WO2013/022974
PCT Pub. Date: Feb. 14, 2013

(65) Prior Publication Data
US 2014/0193833 A1 Jul. 10, 2014

Related U.S. Application Data

(60) Provisional application No. 61/521,242, filed on Aug. 8, 2011.

(51) Int. Cl.
*G01N 33/574* (2006.01)
*G01N 33/50* (2006.01)

(52) U.S. Cl.
CPC ...... *G01N 33/57407* (2013.01); *G01N 33/5005* (2013.01); *G01N 33/57434* (2013.01); *G01N 33/57438* (2013.01)

(58) Field of Classification Search
CPC .................................................... G01N 33/574
USPC ................................................ 435/7.23, 7.1
See application file for complete search history.

(56) References Cited

U.S. PATENT DOCUMENTS

| | | |
|---|---|---|
| 7,232,653 B1 | 6/2007 | Austrup et al. |
| 2007/0212702 A1 * | 9/2007 | Tomlins et al. ............ 435/6 |
| 2009/0170075 A1 * | 7/2009 | Petrovics et al. ............ 435/6 |
| 2010/0028348 A1 | 2/2010 | Anziano |
| 2010/0248207 A1 | 9/2010 | Raz et al. |
| 2011/0033924 A1 | 2/2011 | Berry et al. |
| 2011/0053152 A1 | 3/2011 | Goldkorn et al. |
| 2011/0111412 A1 | 5/2011 | Tai et al. |
| 2011/0190149 A1 | 8/2011 | Tainsky et al. |

FOREIGN PATENT DOCUMENTS

| | | |
|---|---|---|
| WO | 98/12564 | 3/1998 |
| WO | WO 2010/126972 | * 11/2010 |

OTHER PUBLICATIONS

Wigginton et al. (Analyst, Mar. 22, 2010, 135: 1320-1326).*
Polycarbonate track etch (PCTE) membrane filters (Mar. 25, 2015).*
NCBI-ERG database (Mar. 27, 2015).*
Specimens Collection Procedures (Apr. 2007).*
Supplementary European Search Report dated Jan. 5, 2015 from European Patent Application No. 12821577.9, pp. 1-6.
Desitter, Isabelle et al. A New Device for Rapid Isolation by Size and Characterization of Rare Circulating Tumor Cells. Anticancer Research, Feb. 1, 2011, vol. 31, No. 2, pp. 427-442.
Piaton, Eric et al. Improved Detection of Urothelial Carcinomas with Fluorescence Immunocytochemistry (uCyt+ Assay) and Urinary Cytology: Results of a French Prospective Multicenter Study. Laboratory Investigation, Jun. 1, 2003, vol. 83, No. 6, pp. 845-852.
Mitra, Anirban P. Urine Cytologic Analysis: Special Techniques for Bladder Cancer Detection. Retrieved from the Internet: URL:http://www.dako.com/28229_conn14_urine_cytologic analysis mitra.pdf, Jan. 1, 2010, pp. 169-177.
International Search Report and Written Opinion dated Oct. 15, 2012 from International Application No. PCT/US2012/049997, pp. 1-11.
Budendorf, Lukas et al, Multiprobe FISH for Enhanced Detection of Bladder Cancer in Voided Urine Specimens and Bladder Washings. Am. J. Clin. Pathol., 2001, vol. 116, pp. 79-86.
Hemstreet, III, George P. et al. Biomarker Risk Assessment and Bladder Cancer Detection in a Cohort Exposed to Benzidine. Journal of the National Cancer Institute, Mar. 21, 2001, vol. 93, No. 6, pp. 427-436.
Flezar, Margareta Strojan, Urine and bladder washing cytology for detection of urothelial carcinoma: standard test with new possibilities. Radiol. Oncol., 2010, vol. 44, No. 4, pp. 207-214.
Fujita, Kazutoshi et al. Specific detection of prostate cancer cells in urine by multiplex immunofluorescence cytology. Human Pathology, 2009, vol. 40, pp. 924-933.
Laxman, Bharathi et al. Noninvasive Detection of TMPRSS2:ERG Fusion Transcripts in the Urine of Men with Prostate Cancer. Neoplasia, Oct. 10, 2006, vol. 8, No, 10, pp. 885-888.
Skacel, Marek et al. Validation of a Multicolor Interphase Fluorescence in Situ Hybridization Assay for Detection of Transitional Cell Carcinoma on Fresh and Archival Thin-Layer, Liquid-Based Cytology Slides. Analytical and Quantitative Cytology and Histology, 2001, pp. 381-387.

* cited by examiner

*Primary Examiner* — Yan Xiao
(74) *Attorney, Agent, or Firm* — MH2 Technology Law Group, LLP

(57) ABSTRACT

Provided are methods of using polycarbonate filters to isolate and detect cancer cells in a biological fluid, particularly biological fluids, such as urine, that contain very low concentrations of cancer cells. The characterization of the isolated cells for the presence or absence of cancer specific proteins is useful for cancer diagnosis and prognosis.

17 Claims, 6 Drawing Sheets

SEQUENCE LISTING

```
<160> NUMBER OF SEQ ID NOS: 1

<210> SEQ ID NO 1
<211> LENGTH: 479
<212> TYPE: PRT
<213> ORGANISM: Homo sapiens

<400> SEQUENCE: 1

Met Ala Ser Thr Ile Lys Glu Ala Leu Ser Val Val Ser Glu Asp Gln
1               5                   10                  15

Ser Leu Phe Glu Cys Ala Tyr Gly Thr Pro His Leu Ala Lys Thr Glu
            20                  25                  30

Met Thr Ala Ser Ser Ser Ser Asp Tyr Gly Gln Thr Ser Lys Met Ser
        35                  40                  45

Pro Arg Val Pro Gln Gln Asp Trp Leu Ser Gln Pro Pro Ala Arg Val
    50                  55                  60

Thr Ile Lys Met Glu Cys Asn Pro Ser Gln Val Asn Gly Ser Arg Asn
65                  70                  75                  80

Ser Pro Asp Glu Cys Ser Val Ala Lys Gly Gly Lys Met Val Gly Ser
                85                  90                  95

Pro Asp Thr Val Gly Met Asn Tyr Gly Ser Tyr Met Glu Glu Lys His
            100                 105                 110
```

```
Met Pro Pro Pro Asn Met Thr Thr Asn Glu Arg Arg Val Ile Val Pro
            115                 120                 125

Ala Asp Pro Thr Leu Trp Ser Thr Asp His Val Arg Gln Trp Leu Glu
        130                 135                 140

Trp Ala Val Lys Glu Tyr Gly Leu Pro Asp Val Asn Ile Leu Leu Phe
145                 150                 155                 160

Gln Asn Ile Asp Gly Lys Glu Leu Cys Lys Met Thr Lys Asp Asp Phe
                165                 170                 175

Gln Arg Leu Thr Pro Ser Tyr Asn Ala Asp Ile Leu Leu Ser His Leu
            180                 185                 190

His Tyr Leu Arg Glu Thr Pro Leu Pro His Leu Thr Ser Asp Asp Val
        195                 200                 205

Asp Lys Ala Leu Gln Asn Ser Pro Arg Leu Met His Ala Arg Asn Thr
    210                 215                 220

Gly Gly Ala Ala Phe Ile Phe Pro Asn Thr Ser Val Tyr Pro Glu Ala
225                 230                 235                 240

Thr Gln Arg Ile Thr Thr Arg Pro Asp Leu Pro Tyr Glu Pro Pro Arg
                245                 250                 255

Arg Ser Ala Trp Thr Gly His Gly His Pro Thr Pro Gln Ser Lys Ala
            260                 265                 270

Ala Gln Pro Ser Pro Ser Thr Val Pro Lys Thr Glu Asp Gln Arg Pro
        275                 280                 285

Gln Leu Asp Pro Tyr Gln Ile Leu Gly Pro Thr Ser Ser Arg Leu Ala
    290                 295                 300

Asn Pro Gly Ser Gly Gln Ile Gln Leu Trp Gln Phe Leu Leu Glu Leu
305                 310                 315                 320

Leu Ser Asp Ser Ser Asn Ser Ser Cys Ile Thr Trp Glu Gly Thr Asn
                325                 330                 335

Gly Glu Phe Lys Met Thr Asp Pro Asp Glu Val Ala Arg Arg Trp Gly
            340                 345                 350

Glu Arg Lys Ser Lys Pro Asn Met Asn Tyr Asp Lys Leu Ser Arg Ala
        355                 360                 365

Leu Arg Tyr Tyr Tyr Asp Lys Asn Ile Met Thr Lys Val His Gly Lys
    370                 375                 380

Arg Tyr Ala Tyr Lys Phe Asp Phe His Gly Ile Ala Gln Ala Leu Gln
385                 390                 395                 400

Pro His Pro Pro Glu Ser Ser Leu Tyr Lys Tyr Pro Ser Asp Leu Pro
                405                 410                 415

Tyr Met Gly Ser Tyr His Ala His Pro Gln Lys Met Asn Phe Val Ala
            420                 425                 430

Pro His Pro Pro Ala Leu Pro Val Thr Ser Ser Ser Phe Phe Ala Ala
        435                 440                 445

Pro Asn Pro Tyr Trp Asn Ser Pro Thr Gly Gly Ile Tyr Pro Asn Thr
    450                 455                 460

Arg Leu Pro Thr Ser His Met Pro Ser His Leu Gly Thr Tyr Tyr
465                 470                 475
```

ISOLATION AND DETECTION OF CANCER CELLS

CROSS-REFERENCE TO RELATED APPLICATIONS

This application is a U.S. National Phase application of PCT/US2012/049997 filed 8 Aug. 2012, which claims the benefit of, and relies on the filing date of, U.S. provisional patent application No. 61/521,242, filed 8 Aug. 2011, the entire disclosure of which is incorporated herein by reference.

GOVERNMENT INTEREST

This invention was made in part with Government support. The Government may have certain rights in the invention.

SEQUENCE LISTING

The instant application contains a Sequence Listing which has been submitted in ASCII format via EFS-Web and is hereby incorporated by reference in its entirety. Said ASCII copy, created on 25 Jul. 2012, is named HMJ124PCT.txt and is 4,452 bytes in size.

BACKGROUND

Prostate cancer (CaP) is the most common malignancy and the second leading cause of cancer deaths in American men. The current clinical methods used for the detection of CaP are the serum prostate specific antigen (PSA) test, and the digital rectal examination (DRE). The PSA test was introduced into clinical practice two decades ago and has led to the detection of CaP at a potentially curable stage. Despite the high sensitivity of the PSA test (about 94%), a significant limitation is the very low specificity (about 20%), which is due to the fact that PSA is not a cancer-specific marker [1]. As a result, the clinical use of the PSA test has sparked controversy over the increased incidence in CaP observed in the U.S., which has led to the "over-diagnosis" and "overtreatment" of CaP [2]. A PSA level greater than/or equal to 4.0 ng/ml represents a clinical decision limit that prompts diagnostic biopsy testing [2]. However, a subset of patients with levels below 4.0 ng/ml may have or will develop CaP, and a large portion (65-75%) with greater than 4.0 ng/ml may have a noncancerous prostate-related disorder [3,4]. To increase the detection sensitivity of CaP, the PSA test is used along with the DRE; however, even when used together, the specificity of the screening procedure remains low, leading to unnecessary diagnostic biopsies (65-75% of all biopsies). The prostate biopsy, which can be painful, stressful and lead to infection, is the primary method used for the diagnostic confirmation of CaP [5].

Ideally a diagnostic biomarker should be detectable through noninvasive routes such as the collection and analysis of bodily fluids, including urine; and by methods that increase both sensitivity and specificity. Prostatic material can be acquired by the shedding of cells into the urine following prostate massage during a DRE [6]. Recently, a growing number of reports have demonstrated the benefit of using post-DRE urine in the diagnosis of CaP by the quantitative analysis of intracellular molecular markers rather than by whole cell visualization [4,7-12]. Other reported approaches for the detection of CaP in urine are cytology-based exploratory methods, such as ThinPre® (Hologic, Bedford, Mass.) filtration [14] or centrifugation methods, such as Cytospin® (Thermo Electron Corporation, Waltham, Mass.) methods [7], [13]. These methods have low sensitivity, which methods cannot reliably detect cancer cells in biological samples containing fewer than about 100 cells.

In centrifugation methods, such as Cytospin® (Thermo Electron Corporation, Waltham, Mass.) methods, centrifugal force is used to isolate and deposit cells on microscope slides. However, many cells can be lost during the centrifugation steps in these methods. Also, the centrifugal force can damage cells or cause them to lose their morphology, thereby preventing their subsequent detection. These methods also require a centrifuge and a unique sample chamber assembly comprising a microscope slide. As reported by Fujita et al., using the Cytospin® (Thermo Electron Corporation. Waltham, Mass.) method, LNCaP cells were detected only 50% of the time when urine samples were spiked with 100 LNCaP cells and no cells were detected when the urine samples were spiked with only 10 LNCaP cells.

ThinPrep® (Hologic, Bedford, Mass.) is a method that was first developed for the preparation of cervical cytology samples but has also been used for FISH analysis of bladder carcinoma in voided urine samples [14]. In the ThinPrep® (Hologic, Bedford, Mass.) method, cells are collected on a filter and then transferred to a microscope slide. Because the filter is not translucent, the cells cannot be detected directly on the filter but rather must be transferred to a microscope slide by gently pressing the filter against the slide. The Thin-Prep® (Hologic, Bedford, Mass.) method is very effective for detecting cancer cells in biological samples containing a large number of cells but is not effective in detecting cancer cells in biological samples containing a limited number of cancer cells, particularly samples having fewer than about 100 cancer cells.

While shown to be beneficial in the detection of other cancers, these urinary cytology methods lack the sensitivity needed for the detection of biological samples containing very few cells of interest.

Another group has recently described a method for detecting circulating tumor cells using a proprietary, parylene filter [19]. The parylene filter is adapted to detect circulating tumor cells in blood, which are primarily tumor cells derived from metastasis. As such, this method is not designed to detect early stage cancer before metastatic progression. In addition, this method uses a formaldehyde-based reagent for fixing the cells in the biological sample, finding that the use of alcohol-based fixatives results in the formation of large aggregates of serum protein that quickly clog the filter and lead to failure of the device. Formaldehyde-based fixatives are more hazardous than alcohol-based fixatives, and formaldehyde can cause substantial autofluorescence, which interferes with the immunofluorescent detection and characterization of cells.

Therefore, other methods are needed to provide a sufficiently sensitive and specific method for the non-invasive detection of cancers in biological samples that contain very low concentrations of cancerous cells.

SUMMARY

The present disclosure provides methods of isolating and detecting cancer cells in a biological fluid, particularly biological fluids, such as urine, that contain very low concentrations of cancer cells.

Accordingly, one aspect is directed to a method of isolating a cancer cell, the method comprising incubating a biological fluid containing the cancer cell with a reagent for fixing cells; and isolating the cancer cell on a filter by passing the biological fluid through the filter, wherein the filter comprises a polycarbonate substrate and a plurality of pores.

In one embodiment, the biological fluid is urine. In another embodiment, the cancer cell is a prostate cancer cell, a bladder cancer cell, a kidney cancer cell, a ureter cancer cell, or a urethra cancer cells. In yet another embodiment, the reagent for fixing cells comprises one or more alcohols, including but not limited to, methyl alcohol, ethyl alcohol, or isopropyl alcohol. In other embodiments, each pore in the plurality of pores has a diameter of about 2 μm to 8 μm. In one embodiment, each pore in the plurality of pores has a uniform diameter of about 2 μm, 3 μm, 4 μm, 5 μm, 6 μm, 7 μm or 8 μm and preferably about 5 μm. In another embodiment, the filter comprises a single layer of polycarbonate substrate and the pores pass straight through the filter. In other embodiments, the method does not include a centrifugation step.

Another aspect is directed to a filter comprising a cancer cell, wherein the filter is obtained through a method of isolating a cancer cell, as discussed in this application.

The cancer cell isolated through the methods discussed in this application can be further used or manipulated. For example, the isolated cancer cell can be detected, counted, or further characterized.

Accordingly, a third aspect is directed to a method of detecting a cancer cell in a biological fluid suspected of containing the cancer cell, the method comprising incubating the biological fluid with a reagent for fixing cells; passing the biological fluid through a filter, such that if the biological fluid contains the cancer cell, the cancer cell is retained on the filter, wherein the filter comprises a polycarbonate substrate and a plurality of pores; washing the filter; incubating the filter with at least one detectable reagent that specifically binds to the cancer cell to form a detectable complex; washing the filter; and detecting the detectable complex directly on the filter, wherein detecting the detectable complex indicates the presence of the cancer cell in the biological fluid.

In one embodiment, the biological fluid is urine. In another embodiment, the cancer cell is a prostate cancer cell, a bladder cancer cell, a kidney cancer cell, a ureter cancer cell, or a urethra cancer cell. In yet another embodiment, the reagent for fixing cells comprises one or more alcohols, including but not limited to, methyl alcohol, ethyl alcohol, or isopropyl alcohol. In other embodiments, each pore in the plurality of pores has a diameter of about 2 μm to 8 μm. In one embodiment, each pore in the plurality of pores has a uniform diameter of about 2 μm, 3 μm, 4 μm, 5 μm, 6 μm, 7 μm or 8 μm and preferably about 5 μm. In another embodiment, the filter comprises a single layer of polycarbonate substrate and the pores pass straight through the filter.

In other embodiments, the at least one detectable reagent comprises at least one antibody that binds to the cancer cell, including, but not limited to, at least one antibody that binds to one of the following human proteins: an Ets Related Gene (ERG) protein, an alpha-methylacyl-CoA racemase (AMACR) protein, a prostate specific antigen (PSA) protein, a nucleolin protein, a phosphatase and tensin homolog (PTEN) protein, a phosphorylated Akt protein, a c-Myc protein, a RAF protein, a p63 protein, a prostate specific membrane antigen (PSMA) protein (also known as FOLH1), a high molecular weight cytokeratin, SPARC, SPINK1, SPOP, BRAF, p53, NCOA2, MAOA, CAMK2N1, COL3A1, CLDN8, HOXC6, TMEFF2, NPY, HPGD, BICD1, OR51E1 (PSGR), (OR51E2) (PSGR2), NEFH, MSMB, CACNA1D, PLA2G7, MYO6, CRISP3, TWIST1, JAG1, PCGEM1, PMEPA1, or LTF.

In one embodiment, the at least one antibody binds to an ERG epitope formed by amino acids 42-66 of SEQ ID NO: 1. In another embodiment, the at least one antibody comprises 1) an antibody that binds to a human ERG3 protein (including N-terminally truncated versions of ERG formed by gene fusions between androgen inducible promoter sequences, such as TMPRSS2, and ERG3), 2) an antibody that binds to a human AMACR protein, and 3) an antibody that binds to a human PSA protein or an antibody that binds to a human NKX3.1 protein.

In another embodiment, the at least one detectable reagent comprises at least one nucleic acid probe for detecting expression of one of the following human genes: Ets Related Gene (ERG), alpha-methylacyl-CoA racemase (AMACR), prostate specific antigen (PSA), nucleolin, phosphatase and tensin homolog (PTEN), Akt, c-Myc, RAF, p63, prostate specific membrane antigen (PSMA; also known as FOLH1), NKX3.1, a gene encoding a high molecular weight cytokeratin, SPARC, SPINK1, SPOP, BRAF, p53, NCOA2, MAOA, CAMK2N1, COL3A1, CLDN8, HOXC6, TMEFF2, NPY, HPGD, BICD1, OR51E1 (also known as PSGR), OR51E2 (also known as PSGR2), NEFH, MSMB, CACNA1D, PLA2G7, MYO6, CRISP3, TWIST1, JAG1, PCGEM1, PMEPA1, or LTF. In another embodiment, the at least one nucleic acid probe comprises 1) a nucleic acid probe for detecting expression of human ERG3, 2) a nucleic acid probe for detecting expression of human AMACR, and 3) a nucleic acid probe for detecting expression of human PSA or a nucleic acid probe for detecting expression of human NKX3.1.

In yet another embodiment, as few as 10 cancer cells can be detected in the biological fluid. In another embodiment, the method is capable of detecting at least about 70% of cancer cells in a sample containing 100 cancer cells. In other embodiments, the method does not include a centrifugation step.

BRIEF DESCRIPTION OF THE DRAWINGS

The accompanying drawings, which are incorporated in and constitute a part of this specification, illustrate certain embodiments, and together with the written description, serve to explain certain principles of the antibodies and methods disclosed herein.

FIG. 4A shows the detection of ERG, AMACR and PSA individually and merged with a DAPI stain. FIG. 4B shows the multiplexed detection of ERG, AMACR, and PSA, with and without a merged DAPI stain.

FIG. 5A shows the multiplexed colorimetric IHC staining of ERG (dark brown, nuclear), AMACR (red, cytoplasmic), and NKX3.1 (blue, nuclear) in VCaP cells. FIG. 5B shows the multiplexed colorimetric IHC staining of AMACR (red, cytoplasmic), and NKX3.1 (blue, nuclear) in LNCaP cells.

FIG. 6A shows a prostate cancer positive specimen with detectable AMACR and PSA staining with and without a merged DAPI stain; post-DRE IHC score 2; low cellularity. FIG. 6B shows a prostate cancer positive specimen with no detectable marker staining with and without a merged DAPI stain; post-DRE IHC score 0; medium cellularity.

DETAILED DESCRIPTION

Figure 1:
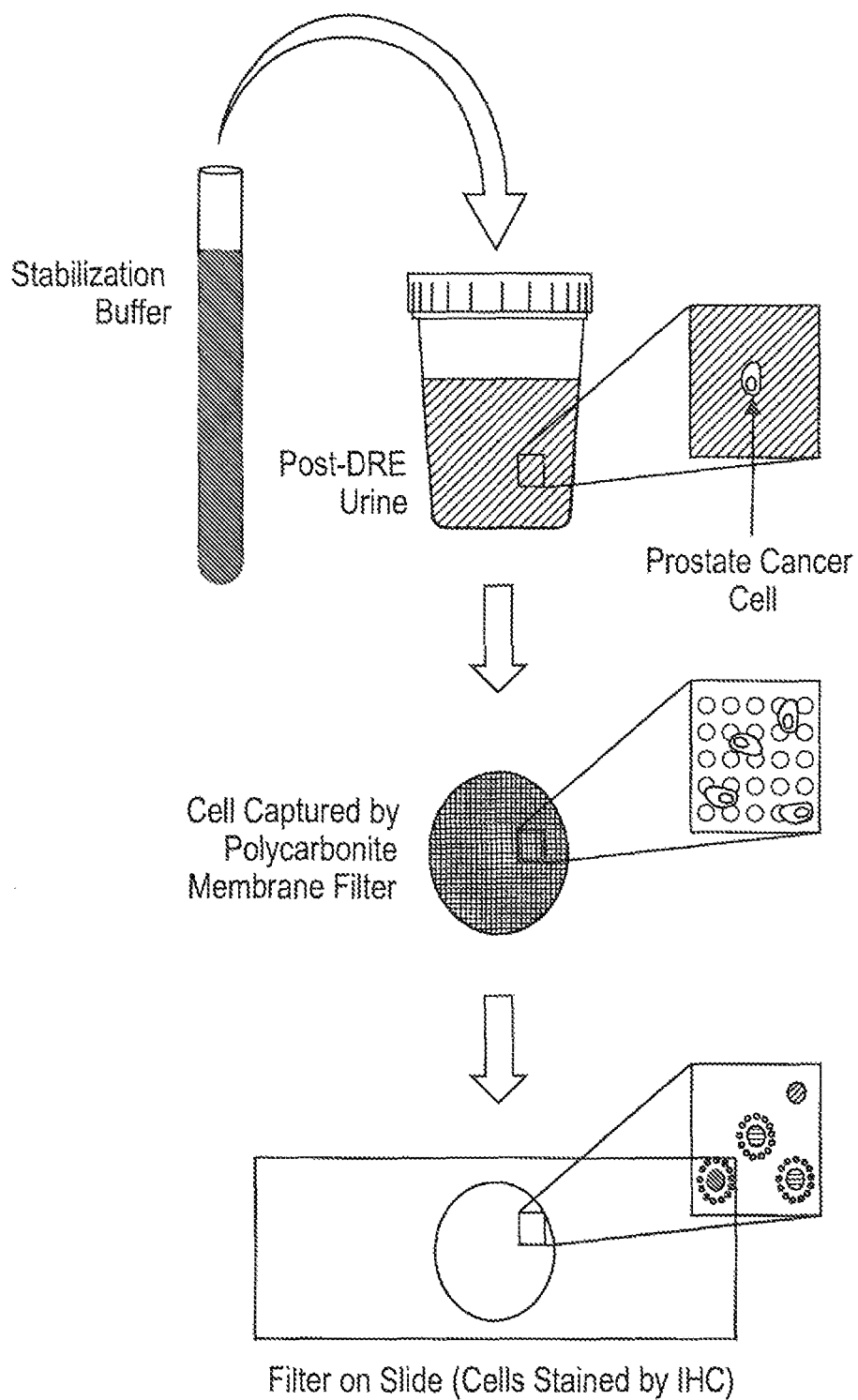
FIG. 1 shows a flowchart of one embodiment of the experimental method. In this embodiment, patient urine is collected post-DRE and stabilized by the addition of Saccomanno's fixative (BBC Biochemical, Mount Vernon, Wash.). Following incubation, the urine specimens are filtered through a polycarbonate filter, which may be secured in a properly sized Swinney filter holder mechanism. After washing, the filters are removed from the holder and transferred to glass microscope slides. To enhance assay sensitivity, the collected cells are maintained and fixed on the filter, which serves as the platform for further immunocytochemical analysis.

Reference will now be made in detail to various exemplary embodiments, examples of which are illustrated in the accompanying drawings. It is to be understood that the following detailed description is provided to give the reader a fuller understanding of certain embodiments, features, and details of aspects of the invention, and should not be interpreted as a limitation of the scope of the invention.

1. Definitions

In order that the present invention may be more readily understood, certain terms are first defined. Additional definitions are set forth throughout the detailed description.

The terms "patient" and "individual" are used interchangeably herein to refer to any mammalian subject for whom diagnosis is desired, particularly humans.

The term "antibody" as used in this disclosure refers to an immunoglobulin or an antigen-binding fragment thereof.

The term "ERG 42-66 epitope" refers to a conformational or linear epitope formed by amino acid residues 42-66 of human ERG3 having the amino acid sequence of ACCESSION NP_891548; VERSION NP_891548.1 GI:33667107, which is hereby incorporated by reference:

```
                                                          (SEQ ID NO: 1)
  1 mastikeals vvsedqslfe caygtphlak temtassssd ygqtskmspr vpqqdwlsqp 61 parvtikmec npsqvngsrn spdecsvakg gkmvgspdtv gmnygaymee khmpppnmtt 121 nerrvivpad ptlwstdhvr qwlewavkey glpdvnillf qnidgkelck mtkddfqrlt 181 psynadills hlhylretpl phltsddvdk alqnsprlmh arntggaafi fpntsvypea 241 tqrittrpdl pyepprrsaw tghghptpqs kaaqpspstv pktedqrpql dpyqilgpts 301 srlanpgsgq iqlwqflllel lsdssnssci twegtngefk mtdpdevarr wgerkskpnm 361 nydklsralr yyydknimtk vhgkryaykf dfhgiaqalq phppesslyk ypsdlpymgs 421 yhahpqkmnf vaphppalpv tsssffaapn pywnsptggi ypntriptsh mpshlgtyy
```

2. Filter

The methods described herein are preferably performed using a polycarbonate filter to isolate cancer cells from a biological fluid or sample. The polycarbonate filter is a permeable filter having pores that can separate cells according to size. The pore size of the filter is selected to retain certain nucleated cells, such as epithelial cells, while allowing the fluid and other debris (e.g., protein aggregates, urinary casts, or ruptured cells) or blood elements (e.g., red blood cells) to flow through the filter.

Preferably, the filter used has a pore size of between 2 μm and 8 μm and a density that is adapted to the selected pore size and which can retain cells while avoiding blockage of the pores during filtration. Preferably, the filter has substantially cylindrical pores with a diameter of about 5 μm and a density in the range $5 \times 10^4$ to $5 \times 10^5$ pores/cm². The filter can also be graded so that all of the pores have a substantially uniform diameter, e.g., about 2 μm, 31 μm, 4 μm, 5 μm, 6 μm, 7 μm or 8 μm.

One example of a filter that can be used in the methods discussed in this application is a hydrophilic, polycarbonate graded filter membrane of the "Track-Etch" type with a pore density of $4 \times 10^5$ pores/cm², a thickness of 10 μm and a pore size of 5 μm, such as that sold by Sterlitech (Kent, Wash.). Other commercial manufacturers of polycarbonate track etch filters include SPI-Pore® (West Chester, Pa.) and Whatman® (Kent, UK). Track-Etch filters are constructed of a single layer of polycarbonate substrate, and the pores pass straight through the filter rather than following a convoluted path through the filter that can capture particles by random entrapment. The Track-Etch polycarbonate filters comprise uniform, cylindrical pores preferentially etched into the membrane, allowing for an even distribution of a collected sample in one plane across the entire exposed membrane surface.

Polycarbonate filters having high pore density (e.g., $5 \times 10^4$ to $5 \times 10^5$ pores/cm²) are translucent and cells isolated on these filters can be detected directly on the filter without having to transfer the cells from the filter to a microscope slide.

Other filter materials known in the art, including, but not limited to, polyimide, polysiloxane, polyester, polyacrylate, cellulose, Teflon, and parylene can also be used as filter substrates.

3. Reagent for Fixing Cells

The methods described in this application involve a step of incubating a biological fluid with a reagent for fixing cells. This step usually takes place before passing the biological fluid through the filter, but in certain embodiments can also occur during or after the step of passing the biological fluid through the filter. Fixing the cells helps to immobilize cellular antigens while retaining cellular and subcellular structure, thereby facilitating the subsequent analysis of the cells.

The reagent for fixing cells includes, but is not limited to, ethyl alcohol, (e.g., about 1%, about 5%, about 10%, about 20%, about 30%, about 40%, about 50% about 60%, about 70%, about 75%, about 80%, about 85%, about 90%, about 95% or about 100% ethyl alcohol), methyl alcohol (e.g., about 1%, about 5%, about 10%, about 20%, about 30%, about 40%, about 50% about 60%, about 70%, about 75%, about 80%, about 85%, about 90%, about 95% or about 100% methyl alcohol), isopropyl alcohol (e.g., about 1%, about 5%, about 10%, about 20%, about 30%, about 40%, about 50% about 60%, about 70%, about 75%, about 80%, about 85%, about 90%, about 95% or about 100% methyl alcohol), acetone; aldehydes and other cross-linking fixatives including, but not limited to, formaldehyde, paraformaldehyde, formalin; zinc formalin, glutaraldehyde; acrolein (acrylic aldehyde); glyoxal (ethanedial, diformyl), malonaldehyde (malonic dialdehyde), diacetyl(2,3-butanedione) and the polyaldehydes; metallic ions and oxidizing agents including, but not limited to, osmium tetroxide and chromic acid (chromium trioxide); picric acid; mercuric chloride; Carnoy's fluid (ethanol, chloroform, acetic acid); and zinc acetate and zinc chloride in Tris-Ca buffer; PreservCyt™ solution (Hologic, Bedford, Mass.)™; Biofix™ prep (Tripath Imaging, NC); Streck Cytospray™ fixative (Streck Laboratories, Omaha Nebr.); or Saccomanno's fixative (BBC Biochemical, Mount Vernon, Wash.). The reagent for fixing cells can be an individual fixative and/or any combination of the fixatives. In one embodiment, the reagent for fixing cells comprises one or more alcohols, such as ethyl alcohol and methyl alcohol or ethyl alcohol, methyl alcohol and isopropyl alcohol. In another embodiment, the reagent for fixing cells does not include an aldehyde or other cross-linking fixative selected from the group consisting of formaldehyde, paraformaldehyde, formalin; zinc formalin, glutaraldehyde; acrolein (acrylic aldehyde); glyoxal (ethanedial, diformyl), malonaldehyde (malonic dialdehyde), diacetyl(2,3-butanedione) and the polyaldehydes.

4. Biological Fluid

The methods described in this application are designed to isolate and detect cells obtained from a biological fluid that contains a very low concentration of cells of interest, such as cancer cells. A biological fluid is a fluid obtained from a biologic environment or any other sample obtained from an individual, including a human or an animal, that is in a fluidic state or is treated in such a way that the sample assumes a fluidic state. Exemplary biologic fluids include, but are not limited to, blood, serum, urine, saliva, sputum, or stool. The sample may also contain tumor-derived exosomes. Exosomes are small (typically 30 to 100 nm) membrane-bound particles that are released from normal, diseased, and neoplastic cells and are present in blood and other bodily fluids. The methods disclosed in this application can be used with samples collected from a variety of mammals, but preferably with samples obtained from a human subject.

5. Cells of Interest

The methods described in this application can be used to isolate or detect any cell of interest in the biological fluid. As noted above, the methods are designed to permit the isolation or detection of cells in a sample that contains a very low number of cells.

In one aspect, the cells of interest to be isolated or detected are cancer cells. In one embodiment, the biological fluid is urine and the cells of interest are cancer cells in the urine. Any cancer cell that is present in the urine can be isolated or detected using the methods described in this application. Exemplary cancer cells that are known to be found in the urine, include but are not limited to, prostate cancer, bladder cancer, kidney cancer, ureter cancer, and urethra cancer.

In one embodiment, the cancer cell is a prostate cancer cell. For isolating or detecting prostate cancer cells, the urine may be collected following a digital rectal examination (DRE) or a prostate biopsy to increase the total number of prostate cells in the urine sample. The detection method may be performed without other tests to determine whether or not a sample contains cancer cells. Alternatively, the detection method may be used with other detection assays to enhance sensitivity. For example, if a first diagnostic test (e.g., PSA test) is positive and the first diagnostic biopsy is negative, the detection methods described in this application can be used to confirm the negative biopsy, if the result of the detection method is negative, or to recommend a second biopsy, if the result of the detection method is positive.

6. Detection of Cells on Filter

The cells isolated on the filter can be detected using any appropriate detection means, including, for example, a microscope. To facilitate detection, the cancer cells are incubated with a detectable reagent that specifically binds to the cancer cells, such as one or more antibodies or one or more nucleic acid probes. The incubation step usually occurs after the cells are isolated on the filter but in certain embodiments can also occur during or before the isolation step. The incubation step can also include one or more detectable reagents that do not specifically bind to the cancer cells and that can be used as a positive control for cells of particular origin. For example, antibodies that bind to prostate epithelium can be used as a positive control for cells of prostatic origin. Exemplary antibodies that bind to prostate epithelium include antibodies that bind to prostate specific antigen (PSA), also known as kallikrein 3 (KLK3), prostate acid phosphatase (PAP), also known as acid phosphatase, prostate (ACPP), NK3 homeobox 1 (NKX3.1), nuclear marker of prostate epithelial cells, p63 (prostate basal cell marker that does not bind prostate cancer; also known as cytoskeleton associated protein 4; CKAP4), high molecular weight cytokeratin (e.g., cytokeratin 1, 2, 3, 4, 5, 6, 10, 14, 15, or 16), or prostate specific membrane antigen (PSMA), also known as folate hydrolase 1 (FOLH1). Non-specific detectable reagents also include dyes that bind to DNA, such as, 4',6-diamidino-2-phenylindole (DAPI), which binds strongly to A-T rich regions of DNA and can be used to identify nucleated cells.

The nucleic acid and amino acid sequences for human PSA, PAP, NKX3.1, p63, and FOLH1 are known. The unique identifier code assigned by Hugo Gene Nomenclature Committee (HGNC) for these genes and their NCBI Reference Sequences are provided in Table 1, which sequences are hereby incorporated by reference in their entirety:

TABLE 1

| Gene | HGNC ID | NCBI Reference |
| --- | --- | --- |
| PSA/KLK3 | HGNC: 6364 | NM_145864.1, GI: 22208991 |
| PAP/ACPP | HGNC: 125 | NM_001099.4, GI: 197116346 |
| NKX3.1 | HGNC: 7838 | NR_046072.1, GI: 373432629 |
| P63/CKAP4 | HGNC: 16991 | NM_006825.3, GI: 219842270 |
| PSMA/FOLH1 | HGNC: 3788 | NM_004476.1, GI: 4758397 |

Antibodies that specifically bind to cancer cells, including but not limited to, prostate cancer, bladder cancer, kidney cancer, ureter cancer, and urethra cancer, are known in the art. For example, antibodies that bind to prostate cancer and can be used as prostate cancer markers, include, but are not limited to, antibodies that bind to the proteins encoded by the ETS-related gene (ERG) (including ERG proteins encoded by fusions between androgen inducible promoter sequences, such as TMPRSS2, and ERG, as discussed in further detail below) or alpha-methylacyl-CoA racemase (AMACR) gene. The overexpression of ERG and AMACR have been associated with prostate cancer, as disclosed in the published patent application US2009/0170075, which application is hereby incorporated by reference in its entirety.

The HGNC has assigned AMACR the unique identifier code: HGNC:451. The AMACR gene encodes a racemase. The NCBI Reference Sequence for AMACR is NM_014324.5, GI:266456114, which sequences are hereby incorporated by reference. The HGNC has assigned ERG the unique identifier code: HGNC:3446. The NCBI Reference Sequences for two isoforms of ERG are transcript variant 1 (also known as ERG3): NM_182918.3, GI:209954798; and transcript variant 2: NM_004449.4, GI:209954801, which sequences are hereby incorporated by reference. The amino acid sequence of ERG transcript variant 1 is the same as the amino acid sequence of human ERG3, as set forth at ACCESSION NP_891548; VERSION NP_891548.1 GI:33667107 (i.e., SEQ ID NO:1). The GenBank reference for a third ERG isoform, transcript variant 8 is AY204742.1, GI:37781336, which sequences are hereby incorporated by reference. ERG-related oncogenic alterations, including the fusion between the androgen receptor regulated prostate associated gene TMPRSS2 and ERG, result in the overexpression of ERG in 50-70% of prostate cancer. Fusion between the TMPRSS2 gene promoter and ERG results in the overexpression of N-terminally truncated or full-length forms of ERG proteins (Klezovitch et al., 2008; Sun et al., 2008). Fusion events between ERG and other androgen inducible promoter sequences, such as SLC45A3 (Han et al., 2008) and NDRG1 (Pflueger et al., 2009), have also been identified in prostate cancer. Analyzing the expression of ERG, thus, includes analyzing the gene fusion products that are associated with prostate cancer, such as TMPRSS2-ERG. As the gene fusion occurs at the 5' end of the ERG nucleic acid sequence and at the N-terminal end of the ERG protein, one of skill in the art can use existing probes or antibodies, or design their own, to detect the ERG gene fusion products.

In addition to detecting prostate cancer, antibodies that bind to ERG can also be used to detect other cancers, including, but not limited to, Ewing sarcoma, acute myeloid leukemia, acute T-lymphoblastic leukemia, colon cancer, or endothelial cancer.

Other prostate cancer markers that can be used to detect prostate cancer include, but are not limited to, SPARC, SPINK1, SPOP, BRAF, p53, NCOA2, MAOA, CAMK2N1, COL3A1, CLDN8, HOXC6, TMEFF2, NPY, HPGD, BICD1, OR51E1 (PSGR), OR51E2 (PSGR2), PSMA (also known as FOLH1), NEFH, MSMB, CACNA1D, PLA2G7, MYO6, CRISP3, TWIST1, JAG1, PCGEM1, PMEPA1, LTF, and ETV1 and ETV4 (other ETS family members, like ERG, that undergo frequent gene fusion with the 5' untranslated region of the androgen-regulated gene TMPRSS2). The nucleic acid and amino acid sequences for these genes are known, as set forth in Table 2, which sequences are hereby incorporated by reference in their entirety:

TABLE 2

| Gene | HGNC ID | NCBI Reference |
| --- | --- | --- |
| SPARC | HGNC: 11219 | NM_003118.3, GI: 365777426 |
| SPINK1 | HGNC: 11244 | NM_031223, GI: 195234783 |

TABLE 2-continued

| Gene | HGNC ID | NCBI Reference |
| --- | --- | --- |
| SPOP | HGNC: 11254 | NM_003563.3, GI: 56119172 |
| BRAF | HGNC: 1097 | NM_004333.4, GI: 187608632 |
| P53 | HGNC: 11998 | NM_000546.5, GI: 371502114 |
| NCOA2 | HGNC: 7669 | NM_006540.2, GI: 76253684 |
| MAOA | HGNC: 6833 | NM_000240.3, GI: 395132502 |
| CAMK2N1 | HGNC: 24190 | NM_018584.5, GI: 115387115 |
| COL3A1 | HGNC: 2201 | NM_000090.3, GI: 110224482 |
| CLDN8 | HGNC: 2050 | NM_199328.2, GI: 297206863 |
| HOXC6 | HGNC: 5128 | NM_153693.3, GI: 100349242 |
| TMEFF2 | HGNC: 11867 | NM_016192.2, GI: 12383050 |
| NPY | HGNC: 7955 | NM_000905.3, GI: 268834883 |
| HPGD | HGNC: 5154 | NM_001256301.1, GI: 372626409 |
| BICD1 | HGNC: 1049 | NM_001714.2, GI: 51039801 |
| OR51E1/PSGR | HGNC: 15194 | NM_152430,3, GI: 205277377 |
| OR51E2/PSGR2 | HGNC: 15195 | NM_030774.3, GI: 218563727 |
| NEFH | HGNC: 7737 | NM_021076.3, GI: 196162718, |
| MSMB | HGNC: 7372 | NM_002443.3, GI: 325910870 |
| CACNAID | HGNC: 1391 | NM_000720.2, GI: 192807296 |
| PLA2G7 | HGNC: 9040 | NM_001168357.1, GI: 270133070 |
| MY06 | HGNC: 7605 | NM_004999.3, GI: 92859700 |
| CRISP3 | HGNC: 16904 | NM_00661.2, GI: 300244559 |
| TWIST1 | HGNC: 12428 | NM_000474.3, GI: 68160957 |
| JAG1 | HGNC: 6188 | NM_000214.2, GI: 168480146 |
| PCGEM1 | HGNC: 30145 | NR_002769.1, GI: : 84872058 |
| PMEPA1 | HGNC: 14107 | NM_020182.4, GI: 364023807 |
| LTF | HGNC: 6720 | NM_002343.3, GI: 312434005 |
| ETV1 | HGNC: 3490 | NM_004956.4, GI: 253683425 |
| ETV4 | HGNC: 3493 | NM_001986.2, GI: 118918427 |

Other cancer-specific antibodies, include, but are not limited to, antibodies that bind to nucleolin (NCL; a nucleolus protein whose overexpression has been implicated in tumorigenesis), phosphatase and tensin homolog (PTEN), phosphorylated Akt (AKT1), c-Myc, or RAF. The nucleic acid and amino acid sequences for these genes are known, as set forth in Table 3, which sequences are hereby incorporated by reference in their entirety:

TABLE 3

| Gene | HGNC ID | NCBI Reference |
| --- | --- | --- |
| NCL | HGNC: 7667 | NM_002443.3, GI: 5596787 |
| PTEN | HGNC: 9588 | NM_000314.4, GI: 110224474 |
| AKT1 | HGNC: 391 | NM_005163.2, GI: 62241010 |
| c-Myc | HGNC: 7553 | NM_002467.4, GI: 239582723 |
| RAF | HGNC: 9829 | NM_002880.3, GI: 189458830 |

Because the biological fluids used in the methods of this application are preferably obtained from a human, the antibodies used in such methods should bind to the human polypeptide of interest.

In one embodiment, the anti-ERG antibody is an antibody that binds to the ERG 42-66 epitope, as disclosed in published PCT application WO 2010/126972, which application is hereby incorporated by reference in its entirety.

In another embodiment, the method of detecting a cancer prostate cell in a sample comprises detecting the expression of one of the following combinations of human genes:
 ERG, AMACR and PSA or NKX3.1;
 ERG, AMACR and CLDN8;
 ERG, CLDN8, and CACNA1D;
 CLDN8, HOXC6, TMEFF2, NPY, and HPGD;
 AMACR, CLDN8, TMEFF2, NPY, and HPGD;
 ERG, CLDN8, CACNA1D, HOXC6, TMEFF2, NPY, and HPGD;
 ERG, CLDN8, CACNA1D, HOXC6, TMEFF2, NPY, and HPGD and at least one of the following human genes: BICD1, OR51E1, OR51E2, FOLH1, and SPARC;

ERG, CLDN8, CACNA1D, HOXC6, TMEFF2, NPY, HPGD, BICD1, OR51E1, OR51E2, FOLH1, and SPARC;

ERG, CLDN8, CACNA1D, HOXC6, TMEFF2, NPY, HPGD, BICD1, OR51E1, OR51E2, FOLH1, and SPARC and at least one of the following human genes: PLA2G7, MYO6, CRISP3, TWIST1, and JAG1;

ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, and JAG1;

ERG, AMACR, CLDN8, TMEFF2, NPY, and HPGD; or

ERG, OR51E1, PCGEM1, PMEPA1, and LTF; CAMK2N1, MAOA, COL3A1, HPGD, and SPARC.

Gene expression can be detected at either the protein or nucleic acid level. If a target gene has multiple splice variants (e.g., ERG), it is possible to design a nucleic acid probe that recognizes a region common to each variant or an antibody that binds to a region common to each protein encoded by the variants and/or to use more than one probe or antibody, each of which may recognize one or more variants.

In certain embodiments, nucleic acids corresponding to the cancer-specific genes, including one or more of the genes identified in Tables 1, 2, or 3, are detected. Detecting a nucleic acid of interest generally involves hybridization between a target (e.g. mRNA or cDNA) and a probe. Sequences of the tissue specific or cancer specific genes are known (see e.g., Tables 1-3). Therefore, one of skill in the art can readily design hybridization probes for detecting those genes. See e.g., Sambrook et al., Molecular Cloning: A Laboratory Manual, 4$^{th}$ Ed., Cold Spring Harbor Press, Cold Spring Harbor, N.Y., 2012. Each probe should be substantially specific for its target, to avoid any cross-hybridization and false positives.

For example, fluorescent in situ hybridization (FISH) analysis is used to detect cancer cells. In these embodiments, nucleic acid probes that bind to tissue-specific and/or cancer-specific genes, including one or more of the genes identified in Tables 1, 2, or 3, are incubated with cells that have been isolated on the filter according to the methods discussed throughout the application. Other known in situ hybridization techniques can be used to detect tissue-specific and/or cancer-specific genes or nucleic acids, including one or more of the genes identified in Tables 1, 2, or 3. The nucleic acid probes (DNA or RNA) can hybridize to DNA or messenger RNA and can be designed to detect nucleic acid alterations in the cancer-specific genes, such as gene fusion events (TMPRSS2-ERG, SLC45A3-ERG, NDRG1-ERG, etc.), amplifications, deletions, or mutations. Other commonly used methods known in the art for the quantification of mRNA expression in a sample include microarrays, northern blotting, RNAse protection assays, and PCR-based methods, such as reverse transcription polymerase chain reaction (RT-PCR) or qPCR. Because the biological fluids used in the methods of this application are preferably obtained from a human, the nucleic acid probes used in such methods should hybridize to the human gene of interest. Nucleic acid detection generally involves hybridization between a target (e.g. a transcript or cDNA) and a nucleic acid probe. Because the nucleic acid sequences of the genes identified above are known, hybridization probes for their detection can readily be designed by a person skilled in the art. Where a target gene has multiple splice variants and it is desired to detect all of them then it is possible to design a nucleic acid probe that recognizes a region common to each variant and/or to use more than one reagent, each of which may recognize one or more variants.

Detecting a nucleic acid of interest generally involves hybridization between a target (e.g. mRNA or cDNA) and a nucleic acid probe. Sequences of the genes used in the prostate cancer gene expression profile are known (see above). Therefore, one of skill in the art can readily design hybridization probes for detecting those genes. See e.g., Sambrook et al., Molecular Cloning: A Laboratory Manual, 4$^{th}$ Ed., Cold Spring Harbor Press, Cold Spring Harbor, N.Y., 2012. Each probe should be substantially specific for its target, to avoid any cross-hybridization and false positives. An alternative to using specific probes is to use specific reagents when deriving materials from transcripts (e.g., during cDNA production, or using target-specific primers during amplification). In both cases specificity can be achieved by hybridization to portions of the targets that are substantially unique within the group of genes being analyzed, e.g. hybridization to the polyA tail would not provide specificity. If a target has multiple splice variants, it is possible to design a hybridization reagent that recognizes a region common to each variant and/or to use more than one reagent, each of which may recognize one or more variants.

Using markers associated with more advanced stage cancer, it is also possible to use the methods discussed in this application to identify advanced stage cancer or to predict adverse outcomes, such as cancer recurrence, metastasis, or even death.

Using detectable reagents, such as antibodies or nucleic acid probes, cancer cells can be detected using standard immunohistochemical or immunocytochemical techniques. To facilitate detection, the detectable reagent may be coupled to a label. The label is detectable by any means, including but not limited to, spectroscopic, photochemical, biochemical, immunochemical, electrical, optical or chemical means. Examples of labels, include but are not limited to a fluorescent compound (including fluorescein, fluorescein isothiocyanate (FITC), rhodamine, 5-dimethylamine-1-naphthalenesulfonyl chloride, phycoerythrin, lanthanide phosphors, or the cyanine family of dyes (such as Cy-3 or Cy-5) and the like); a bioluminescent compound (such as luciferase, green fluorescent protein (GFP), yellow fluorescent protein, etc.); an enzyme that produces a detectable reaction product (such as horseradish peroxidase, β-galactosidase, luciferase, alkaline phosphatase, or glucose oxidase and the like), or a radiolabel (such as $^{3}$H, $^{14}$C, $^{15}$N, $^{35}$S, $^{90}$Y, $^{99}$Tc, $^{111}$In, $^{125}$I, or $^{131}$I). The attachment of a compound to a label can be through any means, including covalent bonds, adsorption processes, hydrophobic and/or electrostatic bonds, as in chelates and the like, or combinations of these bonds and interactions and/or may involve a linking group.

In some embodiments, a detectable reagent, such as an antibody is detected directly by conjugation with a label. In other embodiments, the detectable reagent, such as an antibody is indirectly detected. For example, secondary antibodies are raised against primary antibodies, and the secondary antibody is labeled for detection.

7. Sensitivity

One of the limitations of other known methods for detecting cancer cells, such as the Cytospin® (Thermo Electron Corporation, Waltham, Mass.) methods and the ThinPrep® (Hologic, Bedford, Mass.) methods, is their limited sensitivity. These other methods are not effective in detecting cancer cells in biological samples containing a limited number of cancer cells, particularly samples having fewer than about 100 cancer cells. In contrast, the methods described in this application enhance cell recovery and the sensitivity of detecting cancer cells in a sample approximately 100-fold as compared to existing methods. Using the methods described in this application, it is possible to detect cancer cells 100% of time in a sample containing as few as 10 cancer cells. In addition, using the methods described in this application, it is possible to detect about 70-85%, or more, of cancer cells in a sample containing 100 cancer cells and about 70-80%, or more, of cancer cells in a sample containing 10 cancer cells. The methods described in this application can also be carried out without the use of a centrifugation step, minimizing any damage to the cells caused by centrifugation.

8. Kits

In some embodiments, the components used in the methods described in this application (e.g., filter, detectable reagents, reagent for fixing cells, etc.) are supplied in the form of a kit useful, for example, for performing methods of isolating or detecting cancer cells. In one embodiment, at least one detectable reagent, such as an antibody, is provided in one or more containers, optionally with one or more additional components, including a filter, a reagent for fixing cells, a syringe, a buffer, or a microscope slide. In other embodiments, the at least one detectable reagent, such as an antibody, is provided suspended in an aqueous solution or as a freeze-dried or lyophilized powder, for instance. The container(s) in which at least one detectable reagent is supplied can be any conventional container that is capable of holding the supplied form, for instance, microfuge tubes, ampoules, or bottles.

In other embodiments, control slides upon which are mounted one or more tissue or cell preparations (e.g., biopsy, cell pellets, or cells) that may serve as positive and/or negative controls may be provided in an appropriate and separate container.

In one embodiment, a kit includes instructional materials disclosing methods of use of the kit contents in a disclosed method. The instructional materials may be provided in any number of forms, including, but not limited to, written form (e.g., hardcopy paper, etc.), in an electronic form (e.g., computer diskette or compact disk) or may be visual (e.g., video files). The kits may also include additional components to facilitate the particular application for which the kit is designed. Thus, for example, the kits may additionally include buffers and other reagents routinely used for the practice of a particular method. Such kits and appropriate contents are well known to those of skill in the art.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Materials and Methods

Cell Lines and Cell Recovery.

VCaP cells (ATCC, Manassas, Va., no. CRL-1740), an ERG-positive prostate cancer cell line, were maintained in DMEM (Gibco, Carlsbad, Calif.) medium supplemented with 10% fetal bovine serum (FBS; ATCC). LNCaP cells (ATCC, no. CRL-1740), an ERG-negative prostate cancer cell line, were maintained in RPMI-1640 medium (Gibco, Carlsbad, Calif.) supplemented with 10% FBS, 2.8 mM L-Glutamine (Gibco, Carlsbad, Calif.), and 1.4% penicillin-streptomycin-neomycin antibiotic mixture (Gibco, Carlsbad, Calif.). NCI-H660 cells (ATCC, no. CRL-5813), a prostate cancer cell line, were maintained in RPMI-1640 medium supplemented with 5% FBS, 4 mM L-glutamine, 0.005 mg/ml insulin, 0.01 mg/ml transferrin, 30 nM sodium selenite, 10 nM beta-estradiol, and 10 nM hydrocortisone. All cells were incubated in a 95% air and 5% $CO_2$ humidified atmosphere at 37° C. In controlled spiking experiments, urine samples stored at −80° C. from healthy volunteers were thawed and centrifuged at 3000×g for 15 min. Cells were collected, counted, and diluted to ensure that approximately 10 cells or 100 cells were added to the pre-cleared urine sample. Saccomanno's fixative (BBC Biochemical, Mount Vernon, Wash.) was immediately added in a 1:1 ratio and the samples were incubated at room temperature for a minimum of 2 h. The urine was then filtered, as described below, and stained with DAPI nuclear dye (Invitrogen, Carlsbad, Calif.) for 10 min. The filters were then aspirated completely and covered with round glass coverslips (Electron Microscopy Sciences, Hatfield, Pa.) containing a small drop of Prolong® Gold anti-fade reagent (Invitrogen, Carlsbad, Calif.). Cell number was assessed visually by counting round intact nuclei located on the filter using a Leica DMIRE2 inverted microscope (Leica Microsystems, Bannockburn, Ill.).

Filtration and Immunohistochemistry.

The filtration apparatus was assembled containing a 20 ml 2-part disposable syringe, a 13 mm polypropylene in-line holder, and a 5 µm/13 mm polycarbonate hydrophilic membrane filter (Sterlitech, Kent, Wash.). Approximately 5 ml of 1×TBS (Biocare Medical, LLC., Concord, Calif.) was passed through the filtration apparatus to pre-wet the membrane. After incubation, the urine samples were passed through the membrane filter, which was then flushed through twice with 10 ml 1×TBS. The membrane was then removed from the holder and placed on a Cytoclear glass slide (Sterlitech, Kent, Wash.) and outlined with an Imm-Edge pen (Vector Laboratories, Burlingame, Calif.). Each experimental step was done at room temperature, and 1×TBS was used for all washing between each step.

Example 1

Assay Overview and Optimization

The results from this study demonstrate an enhancement of CaP cell recovery and detection from urine specimens. Prior to developing these detection and isolation methods, we tried to isolate and detect prostate cancer cells in urine samples using the Cytospin® (Thermo Electron Corporation, Waltham, Mass.) and ThinPrep® (Hologic, Bedford, Mass.) methods. However, we could not develop methods for reliably isolating and detecting cancer cells in samples spiked with 10 or 100 cells using the Cytospin® (Thermo Electron Corporation, Waltham, Mass.) and ThinPrep® (Hologic, Bedford, Mass.) methods due to the low sensitivity of these approaches. Thus, through trial and error experimentation, we developed our own method.

Figure 2:
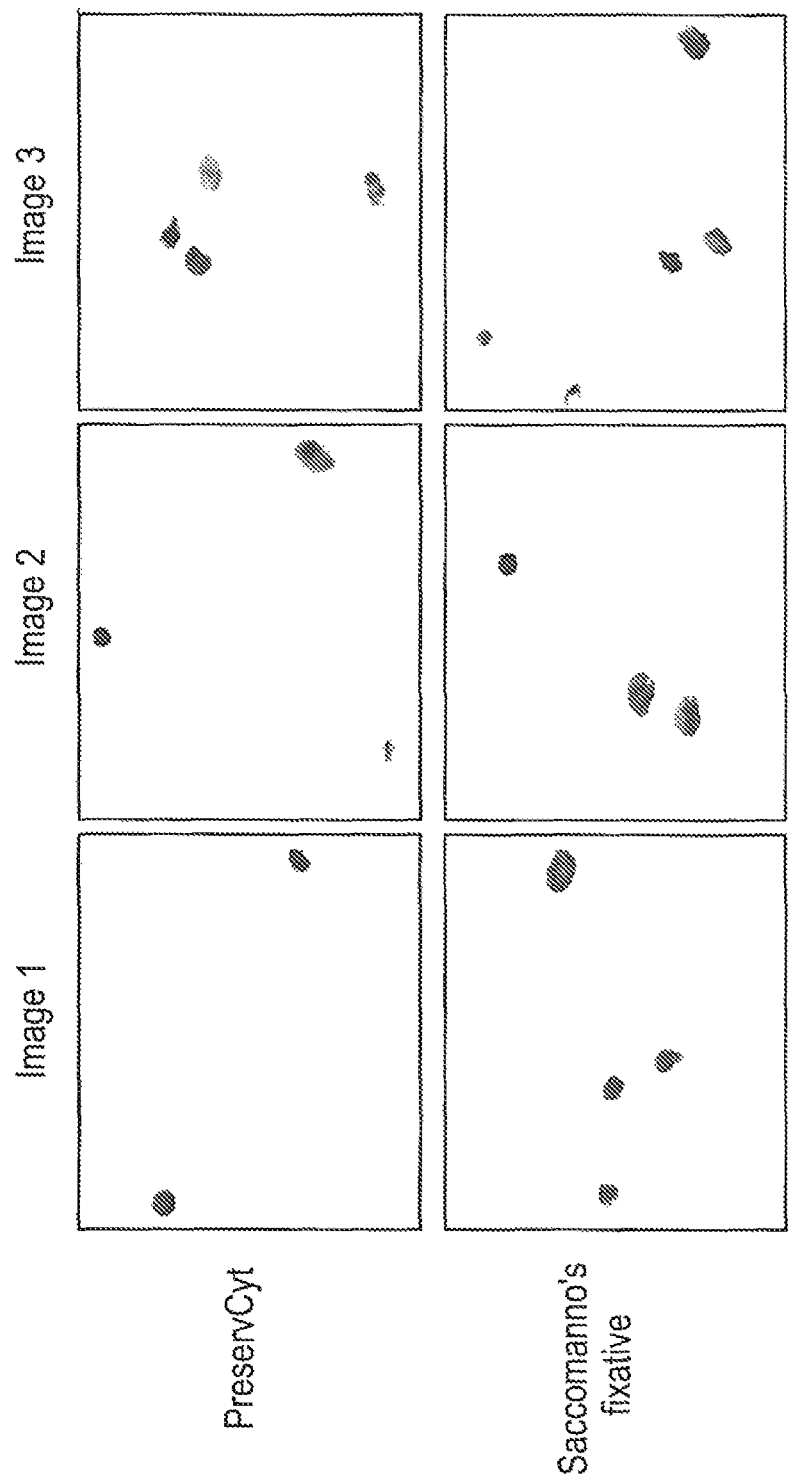
FIG. 2 shows DAPI-stained VCaP cells following incubation with either PreservCyt™ (Hologic, Bedford, Mass.) or Saccomanno's fixative (BBC Biochemical, Mount Vernon, Wash.), indicating that both buffers provide sufficient cell fixation.

Due to the high variability found in urine specimens (i.e. protein content, cellular content, pH, and visible debris) we optimized the biofluid for proper cellular stability and fixation, as well as its ability to pass through the filter pores regardless of debris content, by the use of stabilization buffers. A crude visual scale was formulated ranging from low to high to help assess the debris content of the freshly collected control urine specimens from healthy volunteers. Urine samples can vary from person to person, as well as throughout the day in the same individual. To assess these variables, 10 ml of urine was spiked with VCaP cells, an ERG-positive prostate cancer cell line, and incubated with equal volume of the commercially available buffers, PreservCyt™ (Hologic, Bedford, Mass.) or Saccomanno's fixative (BBC Biochemical, Mount Vernon, Wash.) for up to 4 h at room temperature. Alternatively, an "in-house" buffer containing 50% ethanol and 40 mM Tris-HCl pH 7.0 was tested. Following incubation, the urine was filtered (if possible) through a polycarbonate hydrophilic filter with pore sizes of 2, 5, or 8 μm (Table 1). Once the urine was filtered the collected cells were stained (on the filter) with DAPI nuclear dye, and assessed visually (as described in materials and methods section) for intact nuclear structure, which was indicative of cell stability and fixation by the tested buffer. Both the PreservCyt™ (Hologic, Bedford, Mass.) and Saccomanno's fixative (BBC Biochemical, Mount Vernon, Wash.) offered sufficient cell stability and fixation (FIG. 2), in contrast to the "in-house" buffer, which when visualized, rendered the cells broken and unstable (data not shown).

To determine filter pore size, urine samples with various degrees of debris were assessed for the ability of the debris to pass through, while at the same time preventing the loss of the urine cellular content (summarized in Table 1).

TABLE 4

Stabilization buffer and pore size selection and compatibility

| Visible Urine Debris | Low | Medium | High |
|---|---|---|---|
| Filter Pore Size | 2 micron<br>5 micron<br>8 micron | 5 micron<br>8 micron | 5 micron<br>(depending on fixative)<br>8 micron |
| PreservCyt | Cells fixed; high flow thru rate | Cells fixed; medium flow thru rate | No flow thru |
| Saccomanno's | Cells fixed; high flow thru rate | Cells fixed; high flow thru rate | Cells fixed; medium flow thru rate |

It was determined that low debris content incubated with PreservCyt™ (Hologic, Bedford, Mass.) or Saccomanno's fixative (BBC Biochemical, Mount Vernon, Wash.) passed through all filter pores sizes at a high flow-thru rate. Medium debris containing urine passed through the 8 μm pore filters with ease following incubation with either buffer; however, urine stabilized with Saccomanno's fixative (BBC Biochemical, Mount Vernon, Wash.) had a high flow-thru rate with the 5 μm pore filters, and a medium flow-thru rate with the PreservCyt™ (Hologic, Bedford, Mass.) solution with the 5 μm pores. The high debris urine samples were the determining factor in buffer selection, as only the Saccomanno's fixative (BBC Biochemical, Mount Vernon, Wash.) allowed for the passing of this urine through both the 5 and 8 μm pore filters, in contrast to the PreservCyt™ (Hologic, Bedford, Mass.) solution, which clogged both filters. Thus, the Saccomanno's fixative (BBC Biochemical, Mount Vernon, Wash.) was chosen as the optimal stabilization buffer with the 5 μm pore size allowing filtration of the urine samples with the highest debris content while maintaining maximum cell capture from the urine specimen.

Example 2

Enhancement of Assay Sensitivity

Figure 3:
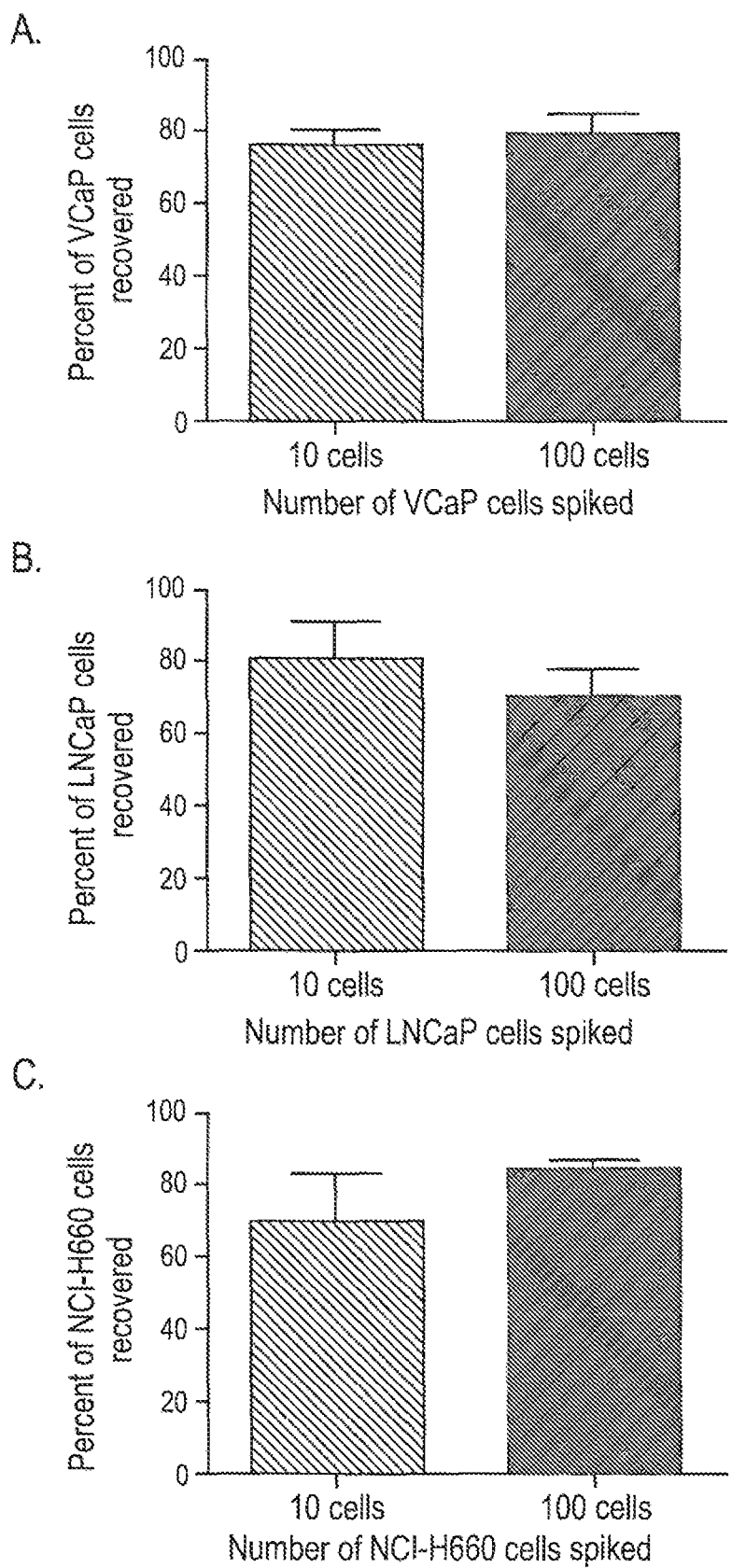
FIG. 3 shows the percentage of VCaP cells (A), LNCaP cells (B), or NCI-H660 cells (C) detected after spiking samples with either 10 or 100 cells.

Assay sensitivity was enhanced by maximizing the percentage of cells recovered following filtration. To test whether our method indeed enhanced cell recovery, over currently reported methods, we spiked low cell numbers (10 or 100 cells) of VCaP or LNCaP (an ERG-negative prostate cancer cell line) cells into centrifuged urine samples, and counted the number of cells left on the filter that were stained positive with DAPI nuclear dye. The VCaP and LNCaP cells were fixed by the addition of Saccomanno's fixative (BBC Biochemical, Mount Vernon, Wash.) at a 1:1 ratio. As shown in FIG. 3, 100% of the time at least 50% of spiked cells were recovered on the filter when as little as 10 cells were spiked into the urine. Specifically, an average of 76% and 79% of VCaP cells (FIG. 3A) were recovered after spiking 10 and 100 cells, respectively; 82% and 72% of LNCaP cells (FIG. 3B) were recovered after spiking 10 and 100 cells, respectively; and 71% and 85% of NCI-H660 cells (FIG. 3C) were recovered after spiking 10 and 100 cells, respectively.

Example 3

Enhancement of Assay Specificity

Visualizing and assessing the protein expression of various prostate cancer- and normal prostate-specific genes in cells (on an individual basis) greatly enhanced the specificity of this assay. Using the membrane filter as the platform for immunocytochemistry, we were able to examine the captured cells for the protein expression of ERG, AMACR, and PSA individually (FIG. 4A) and multiplexed (FIG. 4B) by IHC detection.

For single antibody detection, filters were rinsed briefly followed by a peroxidase block for 5 min using Peroxidase 1 (Biocare, Concord, Calif.). A 10 min protein block using Background Punisher (Biocare, Concord, Calif.) was conducted followed by incubation with primary antibody for 30 min using mouse monoclonal ERG (Center for Prostate Disease Research, Rockville, Md.), rabbit polyclonal AMACR (Biocare, Concord, Calif.), or mouse monoclonal PSA (Biocare, Concord, Calif.). The filters were washed and incubated in secondary antibody (Biocare, Concord, Calif.) for 30 min. The chromogens used for each antibody were as follows: Betazoid DAB chromogen kit (Biocare, Concord, Calif.) was used for ERG, the Vulcan Red chromogen kit (Biocare, Concord, Calif.) for AMACR, and the Ferangi Blue chromogen kit (Biocare, Concord, Calif.) for PSA, were used and incubated on the filters for 30 min. Next, nuclei were stained using DAPI nuclear dye (Invitrogen, Carlsbad, Calif.) diluted 1:3000 in 1×TBS for 5 min. The DAPI stain was removed and the filter rinsed briefly followed by mounting with ProLong® Gold (Invitrogen, Carlsbad, Calif.) mounting medium.

Figure 4:
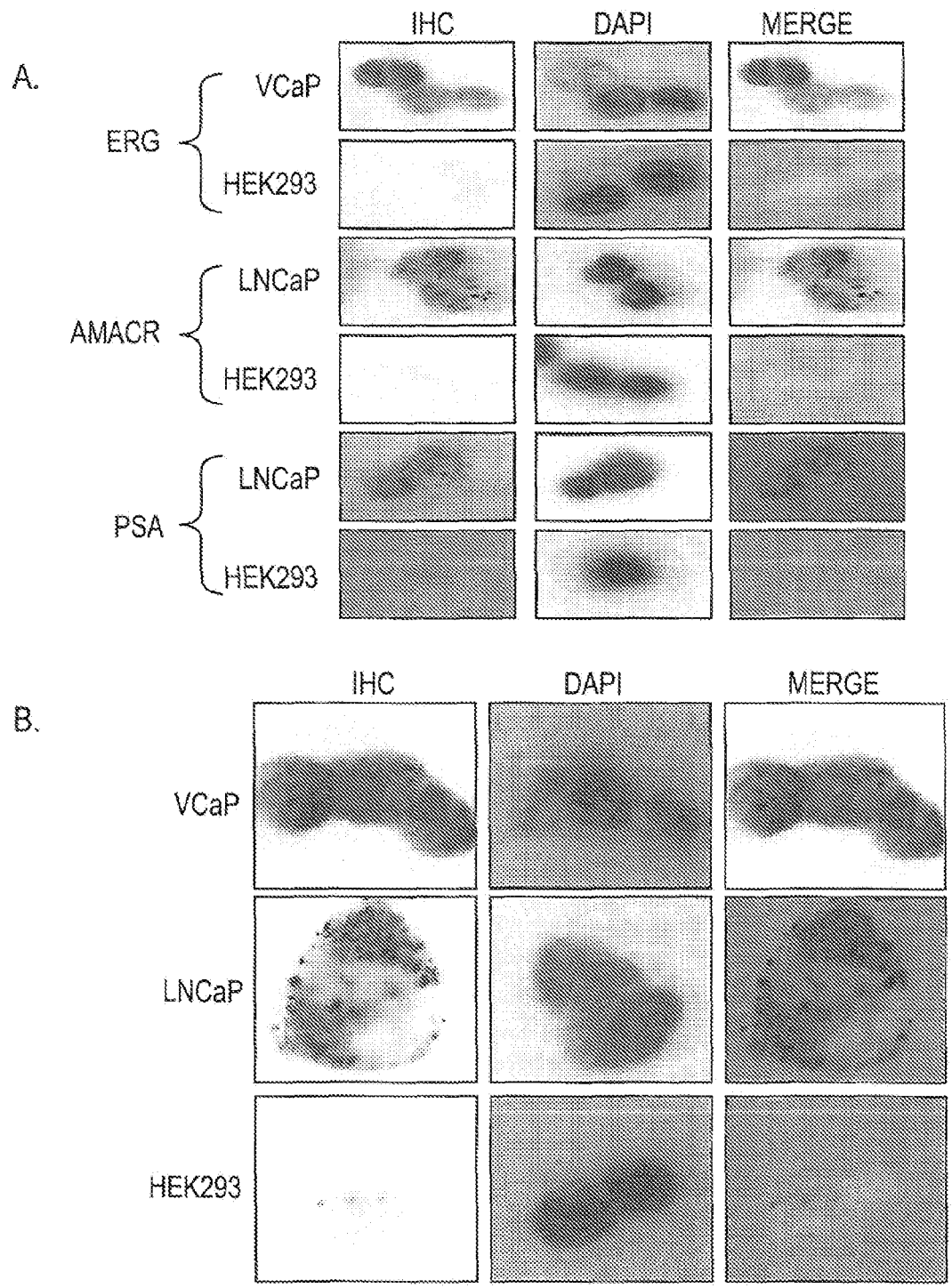
FIG. 4 shows the immunohistochemical detection of prostate cancer-specific proteins in VCaP and LNCaP cells. HEK293 cells were used as a negative control.

FIG. 4A shows the individual colorimetric IHC labeling of ERG, AMACR, and PSA expression. Using human embryonic kidney (HEK293) cells as the negative control for each antibody stain, the expression of ERG protein (brown) in the prostate cancer cell line, VCaP, was localized to the nucleus of the cells. FIG. 4A (top panel). The nuclei are indicated by DAPI staining, shown in the middle column. The exclusive nuclear localization of ERG is confirmed by the merged image in the far right panel, where the brown nuclear stain co-localizes with DAPI. No ERG staining is observed in the HEK293 cells. The prostate cancer specific protein, AMACR (red), is observed in a punctate staining pattern in the cytoplasm of the prostate cancer cells, LNCaP, which is absent in the HEK293 control cells. The expression of PSA (blue) in the cytoplasm of the LNCaP cells is also exclusively expressed, as the HEK293 cells do not express PSA. Notably, the staining intensity was variable within cell lines for each protein detected.

To enhance the clinical applicability and feasibility of the assay, a protocol that enables the simultaneous detection (or lack thereof) of ERG, AMACR and PSA was developed. For detecting multiple antibodies, filters were rinsed briefly followed by a peroxidase block for 10 min using Peroxidase 1 (Biocare, Concord, Calif.). A 10 min protein block using Background Punisher (Biocare, Concord, Calif.) was conducted followed by incubation with ERG/AMACR primary antibody for 30 min. The filters were washed and incubated in MACH 2™ Double Stain 2 secondary antibody (Biocare, Concord, Calif.) for 30 min. To develop the antibody specific color, Betazoid DAB chromogen (Biocare, Concord, Calif.) was prepared according to the manufacturer and incubated on the filters for 30 min. After a quick rinse, Vulcan Red chromogen (Biocare, Concord, Calif.) was prepared according to the manufacturer, and incubated on the filter for 30 min. The chromogen was removed and the filter rinsed. Next, the membrane was incubated in Denaturing solution (Biocare, Concord, Calif.) at a 1:4 ratio for 3 min, followed by three washes in de-ionized water. The filter was then incubated with PSA primary antibody cocktail for 30 min at room temperature, rinsed, and incubated with MACH 2™ (Biocare, Concord, Calif.) mouse-AP secondary antibody for 30 minutes. Ferangi blue chromogen (Biocare, Concord, Calif.) was prepared according to manufacturer, and applied to the membrane for 30 min. The final chromogen application was removed, the filter was washed with 1×TBS once, and the nucleus was stained using DAPI nuclear dye (Invitrogen, Carlsbad, Calif.) diluted 1:3000 in 1×TBS for 5 min. The DAPI stain was removed and the filter rinsed briefly followed by mounting with ProLong® Gold (Invitrogen, Carlsbad, Calif.) mounting medium. The slides were allowed to set before examination under the microscope.

As shown in FIG. 4B, we were able to detect ERG (brown nuclear stain), AMACR (punctate red cytoplasmic stain) and PSA (blue cytoplasmic stain) expression in the VCaP cells, AMACR and PSA in the LNCaP cells, and no expression at all in the HEK293 cells.

Example 4

Triple Stain IHC Protocol with ERG, AMACR, and NKX3.1

VCaP (ERG positive) and LNCaP (ERG negative) were spiked into centrifuged urine samples and incubated with Saccomanno's fixative (BBC Biochemical, Mount Vernon, Wash.) at a 1:1 ratio, as discussed previously. Following incubation, the urine was passed through a 5 µm polycarbonate hydrophilic filter (Sterlitech, Kent, Wash.). The filters were adhered to a Cytoclear microscope slide (Sterlitech, Kent, Wash.), and the slides were kept in TBS wash buffer at 4° C. prior to staining for the prostate cancer markers, ERG and AMACR, and the prostate epithelial marker, NKX3.1.

The slides were stained according to the following protocol. The slides were first rinsed in deionized (DI) water followed by heat pretreatment in Reveal Decloaker (Biocare, Concord, Calif.) solution using the Decloaking Chamber™ Plus (Biocare, Concord, Calif.). The slides were placed into 1× Reveal Decloaker (Biocare, Concord, Calif.) solution at room temperature in a Coplin jar and pretreated at 80° C. for 30 minutes. After 30 minutes, the slides were gently washed by gradually adding DI water into the Coplin jar until the Reveal Decloaker (Biocare, Concord, Calif.) solution was washed out. Next, the slides were immersed into 1×TSBS wash buffer for 2-5 minutes. A peroxidase block was not used.

The slides were incubated in 200 µl of Background Punisher (Biocare, Concord, Calif.) solution for 10 minutes at room temperature and rinsed in TBS wash buffer before adding 200 µl of an ERG/AMACR primary antibody cocktail and incubating for 30 minutes at room temperature. After incubating with the antibody cocktail, the slides were washed in TBS wash buffer for 3 minutes. Next, the slides were incubated in MACH2™ (Biocare. Concord, Calif.) Double Stain 2 secondary antibody (anti-mouse-alkaline phosphatase and anti-rabbit-horseradish peroxidase) for 30 minutes at room temperature followed by a wash in TBS wash buffer for 3 minutes.

A drop of Warp Red™ (Biocare, Concord, Calif.) chromogen was mixed with 2.5 ml of Warp Red™ (Biocare, Concord, Calif.) buffer. 200 µl of Warp Red™ (Biocare, Concord, Calif.) mixture was applied to the filter for 5-10 minutes at room temperature, followed by a wash in TBS wash buffer for 3 minutes. A drop of Deep Space Black™ (Biocare, Concord, Calif.) chromogen was added to 1 ml of Deep Space Black™ (Biocare, Concord, Calif.) buffer and mixed well. The Deep Space Black™ (Biocare, Concord, Calif.) mixture was applied to the filter for 5 minutes at room temperature, followed by a wash in TBS wash buffer for 3 minutes.

The Denaturing solution (Biocare, Concord, Calif.) was diluted 1:4 and applied to the filter for 3 minutes at room temperature. The slides were then washed in TBS wash buffer for 3 minutes. Next the slides were incubated with 200 µl of NKX3.1 (1:100 in Renoir Red (Biocare, Concord, Calif.) diluent) primary antibody for 30 minutes at room temperature. The slides were washed again with TBS wash buffer for 3 minutes before applying MACH2™ (Biocare, Concord, Calif.) secondary antibody (anti-rabbit-alkaline phosphatase) for 30 minutes at room temperature, followed by another wash in TBS wash buffer for 3 minutes.

Next, 1 drop of Ferangi Blue chromogen (Biocare, Concord, Calif.) was mixed with 2.5 ml of Ferangi Blue buffer (Biocare, Concord, Calif.). 200 µl of the Ferangi Blue mixture was applied to the filter for 5-10 minutes at room temperature. The slides were rinsed with DI water (no counterstains were used). The slides were allowed to air dry at room temperature before mounting a coverslip on the slide using EcoMount (Biocare, Concord, Calif.) mounting medium. The slides were dried at room temperature and before examination under a microscope.

Figure 5:
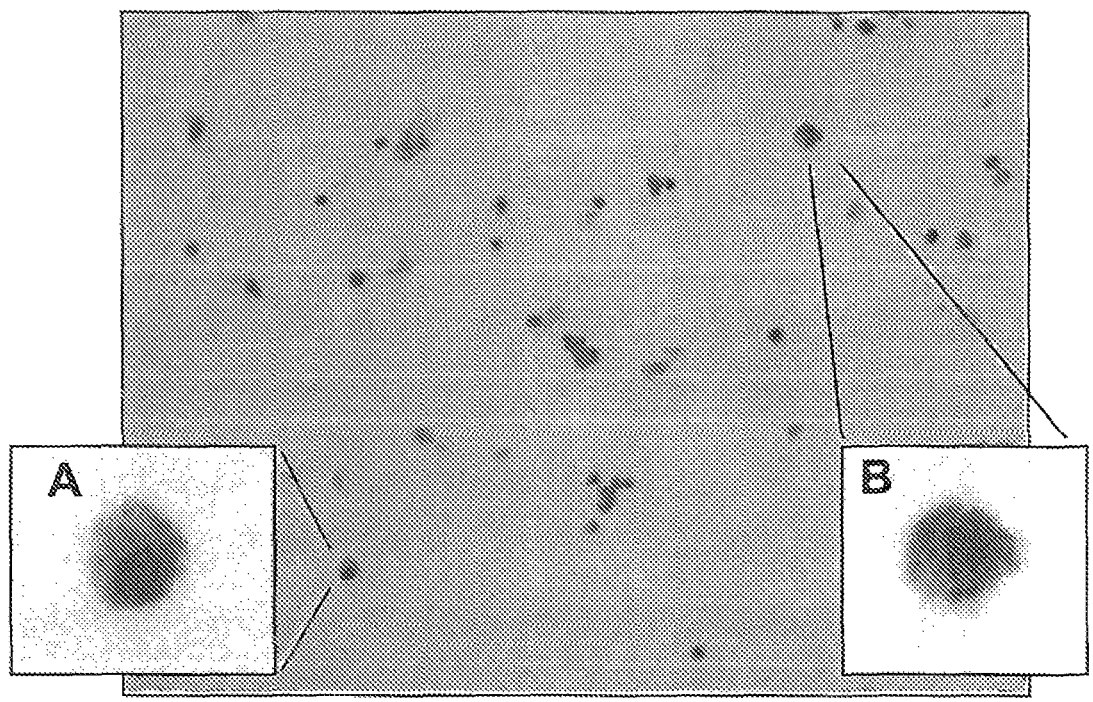
FIG. 5 shows the multiple colorimetric immunohistochemical (IHC) staining of the ERG, AMACR, and NKX3.1 proteins in VCaP and LNCaP cells.

As shown in FIG. 5, the ERG and AMACR markers were detected in the ERG-positive VCaP cells (inset A), and AMACR and NXK3.1 were detected in the ERG-negative LNCaP cells (inset B).

Example 5

Detection of Prostate Cancer Cells in Post-DRE Urine Samples

Urine specimens were collected from 10 patients following a digital rectal exam (DRE). The post-DRE urine specimens were stabilized by the addition of Saccomanno's fixative at a 1:1 ratio. In the meantime, a 5 µm polycarbonate hydrophilic filter (Sterlitech, Kent, Wash.) was pre-wet with 5 ml of 1×TBS. Following incubation, the urine specimens were passed through the polycarbonate filter, and the filters were washed 2 times with 5-10 ml of 1×TBS. The filters were adhered to a Cytoclear microscope slide (Sterlitech, Kent, Wash.), and the slides were kept in 1×TBS wash buffer prior to staining for the prostate cancer markers, ERG and AMACR, and the prostate epithelial marker, NKX3.1.

The slides were stained according to the following protocol. The TBS wash buffer was gently aspirated from the filter. Then 100 µl of Peroxidase 1 solution was added to each filter for 10 minutes at room temperature in a humidified chamber, followed by a quick rinse of the filter with 1×TBS wash buffer.

The slides were incubated in 200 µl of Background Punisher (Biocare, Concord, Calif.) solution for 10 minutes at room temperature and rinsed in TBS wash buffer before adding 200 µl of an ERG/AMACR primary antibody cocktail and incubating for 30 minutes at room temperature. After incubating with the antibody cocktail, the slides were rinsed in TBS wash buffer 2 times. Next, the slides were incubated in MACH2™ (Biocare, Concord, Calif.) Double Stain 2 secondary antibody (anti-mouse-alkaline phosphatase and anti-rabbit-horseradish peroxidase) for 30 minutes at room temperature followed by a quick rinse in TBS wash buffer (3 times).

A drop (32 µl) of Warp Red™ (Biocare, Concord, Calif.) chromogen was mixed with 2.5 ml of Warp Red™ (Biocare, Concord, Calif.) buffer. 200 µl of Warp Red™ (Biocare, Concord, Calif.) mixture was applied to the filter for 20 minutes at room temperature, followed by a quick rinse in TBS wash buffer (5 times). A drop (32 µl) of Betazoid DAB (Biocare, Concord, Calif.) chromogen was added to 1 ml of Betazoid DAB (Biocare, Concord, Calif.) buffer and mixed well. The Betazoid DAB (Biocare, Concord, Calif.) mixture was applied to the filter for 30 minutes at room temperature, followed by a quick rinse in TBS wash buffer for (2 times).

The Denaturing solution (Biocare. Concord, Calif.) was diluted 1:4, according to the manufacture's protocol, and applied to the filter for 3 minutes at room temperature. The slides were then washed 3 times in 1×TBS. Next the slides were incubated with 50 µl of PSA primary antibody cocktail for 30 minutes at room temperature. The slides were quickly rinsed 2 times with TBS wash buffer before applying MACH2™ (Biocare, Concord, Calif.) secondary antibody (anti-mouse-alkaline phosphatase) for 30 minutes at room temperature, followed by 2 quick rinses in TBS wash buffer.

Next, 1 drop (32 µl) of Ferangi Blue chromogen (Biocare, Concord, Calif.) was mixed with 2.5 ml of Ferangi Blue buffer (Biocare, Concord, Calif.). 200 µl of the Ferangi Blue mixture was applied to the filter for 30 minutes at room temperature. The slides were rinsed twice in TBS. Next DAPI (a fluorescent stain that binds strongly to A-T rich regions of DNA) was added to the filters, diluted 1:2000 in deionized water, and incubated for 5 minutes, followed by a quick rinse with deionized water (2 times). Coverslips were mounted on the slide using Prolong® Gold (Invitrogen, Concord, Calif.) anti-fade reagent. The slides were dried at room temperature prior to examination under a microscope.

Figure 6:
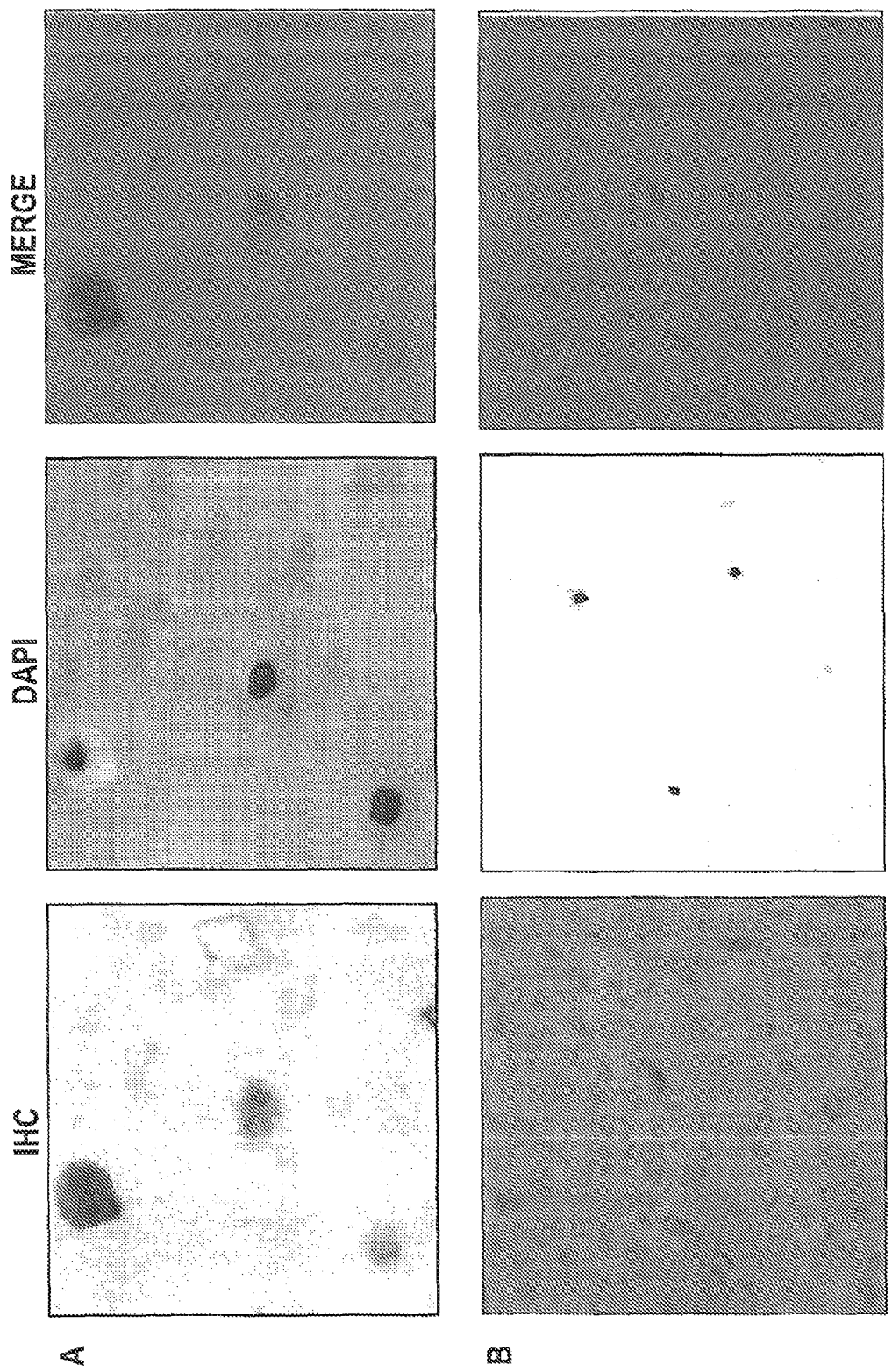
FIG. 6 shows the multiple colorimetric immunohistochemical (IHC) staining of the ERG, AMACR, and NKX3.1 proteins in clinical post-DRE urine specimens.

Notwithstanding the low number of prostate cells in the urine samples following DRE, this post DRE IHC assay successfully detected prostate cells in the urine samples. As shown in FIG. 6, this multiplexed IHC staining protocol was able to distinguish between positive and negative prostate cancer specimens. For example, detecting the AMACR and PSA markers identified a prostate cancer positive specimen (FIG. 6A), whereas detecting no marker staining identified a prostate cancer negative specimen (FIG. 6B).

The post-DRE IHC assay results were evaluated (before the diagnostic biopsy results became available) by using a scoring system based on the expression of the three protein markers as set forth in the table below:

| Postive CaP Markers | PSA Status | Score |
|---|---|---|
| 2 | Positive | 4 |
| 2 | Negative | 3 |
| 1 | Positive | 2 |
| 1 | Negative | 1 |
| 0 | Positive | 0 |
| 0 | Negative | 0 |

The post-DRE IHC assay results showed a promising correlation (8 of 10) with the diagnostic biopsy results, as shown in the table below:

| Sample | Specimen Cellularity | Assay Score | Assay Result | Biopsy Result | Age | Race | PSA ng/ml |
|---|---|---|---|---|---|---|---|
| 1 | High (>2000) | 4 | Positive | Positive | 78 | W | 8.2 |
| 2 | High (>2000) | 4 | Positive | Positive | 73 | A | 17.31 |
| 3 | Medium (720) | 1 | Negative | Negative | 76 | W | 2.1 |
| 4 | Low (23) | 2 | Positive | Positive | 65 | A | 7.8 |
| 5 | Medium (190) | 0 | Negative | Negative | 61 | B | 5 |
| 6 | Medium (120) | 0 | Negative | Negative | 50 | W | 4.93 |
| 7 | Medium (160) | 2 | Positive | Negative | 49 | B | 1.7 |
| 8 | Medium (700) | 1 | Negative | Negative | 64 | W | 4.87 |
| 9 | Medium (580) | 2 | Positive | Negative | 71 | B | 1.4 |
| 10 | High (~2000) | 0 | Negative | Negative | 58 | B | 4.59 |

The three positive biopsy results were also positive by the post-DRE IHC assay. The post DRE IHC assay detected prostate cancer cells in two patients with negative biopsy results. These patients are being followed for re-biopsy results because about 20% of re-biopsies turn out positive for prostate cancer. Notably, the post DRE IHC assay showed no prostate cancer in four patients with PSA scores slightly elevated above 4.0 ng/ml (4.59, 4.87, 4.93, and 5), the level which prompts diagnostic biopsy testing. Thus, the detection methods described in this application can help to reduce the number of unnecessary diagnostic biopsies triggered by PSA levels above 4 ng/ml.

The methods described in this study enhance CaP cell recovery, and therefore enhances the sensitivity of the assay, by significantly increasing cell recovery from post-DRE urine specimens over the currently reported methods [7]. Assay specificity is also enhanced by using a whole cell IHC-based approach for the unambiguous detection of CaP.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

REFERENCES

The following references are cited in the application and provide general information on the field of the invention and provide assays and other details discussed in the application. The following references are incorporated herein by reference in their entirety.
1. Punglia, R. S. et al. (2003) Effect of verification bias on screening for prostate cancer by measurement of prostate-specific antigen. *N Engl J Med* 349, 335-42.
2. Sturgeon, C. M. et al. (2008) National Academy of Clinical Biochemistry laboratory medicine practice guidelines for use of tumor markers in testicular, prostate, colorectal, breast, and ovarian cancers. *Clin Chem*, 54, e11-79.
3. Catalona, W. J. et al. (1991) Measurement of prostate-specific antigen in serum as a screening test for prostate cancer. *N Engl J Med*, 324, 1156-61.
4. Groskopf, J. et al. (2006) APTIMA PCA3 molecular urine test: development of a method to aid in the diagnosis of prostate cancer. *Clin Chem*, 52, 1089-95.
5. Madden, T. et al. (2011) Infective complications after transrectal ultrasound-guided prostate biopsy following a new protocol for antibiotic prophylaxis aimed at reducing hospital-acquired infections. *BJU Int*.
6. Bologna, M. et al. (1988) Early diagnosis of prostatic carcinoma based on in vitro culture of viable tumor cells harvested by prostatic massage. *Eur Urol*, 14, 474-6.
7. Fujita, K. et al. (2009) Specific detection of prostate cancer cells in urine by multiplex immunofluorescence cytology. *Hum Pathol*, 40, 924-33.
8. Laxman, B. et al. (2006) Noninvasive detection of TMPRSS2:ERG fusion transcripts in the urine of men with prostate cancer. *Neoplasia*, 8, 885-8.
9. Rice, K. R. et al. (2010) Evaluation of the ETS-related gene mRNA in urine for the detection of prostate cancer. *Clin Cancer Res*, 16, 1572-6.
10. Rigau, M. et al. (2010) PSGR and PCA3 as biomarkers for the detection of prostate cancer in urine. *Prostate*, 70, 1760-7.
11. van Gils, M. P. et al. (2007) The time-resolved fluorescence-based PCA3 test on urinary sediments after digital rectal examination; a Dutch multicenter validation of the diagnostic performance. *Clin Cancer Res*, 13, 939-43.
12. Whitman, E. J. et al. (2008) PCA3 score before radical prostatectomy predicts extracapsular extension and tumor volume. *J Urol*, 180, 1975-8; discussion 1978-9.
13. Bubendorf, L. et al. (2001) Multiprobe FISH for enhanced detection of bladder cancer in voided urine specimens and bladder washings. *Am J Clin Pathol*, 116, 79-86.
14. Skacel, M. et al. (2001) Validation of a multicolor interphase fluorescence in situ hybridization assay for detection of transitional cell carcinoma on fresh and archival thin-layer, liquid-based cytology slides. *Anal Quant Cytol Histol*, 23, 381-7.
15. Furusato, B. et al. (2010) ERG oncoprotein expression in prostate cancer, clonal progression of ERG-positive tumor cells and potential for ERG-based stratification. *Prostate Cancer Prostatic Dis*, 13, 228-37.
16. Petrovics, G. et al. (2005) Frequent overexpression of ETS-related gene-1 (ERG1) in prostate cancer transcriptome. *Oncogene*, 24, 3847-52.
17. Tomlins, S. A. et al. (2005) Recurrent fusion of TMPRSS2 and ETS transcription factor genes in prostate cancer. *Science*, 310, 644-8.
18. Nguyen, P. N. et al. (2011) A panel of TMPRSS2:ERG fusion transcript markers for urine-based prostate cancer detection with high specificity and sensitivity. *Eur Urol*, 59, 407-14.
19. Lin, H., et al. (2010) Portable Filter-Based Microdevice for Detection and Characterization of Circulating Tumor Cells. *Clinical Cancer Research*, 16(20), 5011-18.

What is claimed:

1. A method of detecting a prostate cancer cell in a biological fluid suspected of containing the prostate cancer cell, the method comprising:
    incubating the biological fluid with a reagent for fixing cells;
    passing the biological fluid through a filter, such that if the biological fluid contains the prostate cancer cell, the prostate cancer cell is retained on the filter, wherein the filter is a translucent filter comprising a polycarbonate substrate and a plurality of pores;
    washing the filter; incubating the filter with at least one detectable reagent that binds to the prostate cancer cell to form a detectable complex; washing the filter; and detecting the detectable complex directly on the filter, wherein detecting the detectable complex indicates the presence of the prostate cancer cell in the biological fluid, wherein the method is capable of detecting a prostate cancer cell in a biological fluid containing not more than 100 prostate cancer cells, wherein the biological fluid is urine.

2. The method of claim 1, wherein the reagent for fixing cells comprises one or more alcohols.

3. The method of claim 2, wherein the one or more alcohols comprise one or more of methyl alcohol, ethyl alcohol, and isopropyl alcohol.

4. The method of claim 1, wherein each pore in the plurality of pores has a diameter of about 2 μm to 8 μm.

5. The method of claim 1, wherein the filter comprises a single layer of polycarbonate substrate and the pores pass straight through the filter.

6. The method of claim 1, wherein the at least one detectable reagent is at least one antibody or at least one nucleic acid probe.

7. The method of claim 6, wherein the at least one antibody binds to one of the following human proteins: an Ets Related Gene (ERG) protein, an alpha-methylacyl-CoA racemase (AMACR) protein, a prostate specific antigen (PSA) protein, a nucleolin protein, a phosphatase and tensin homolog (PTEN) protein, a phosphorylated Akt protein, a c-Myc protein, a RAF protein, a p63 protein, a prostate specific membrane antigen (PSMA) protein, a NKX3.1 protein, a high molecular weight cytokeratin, a SPARC protein, a SPINK1 protein, a SPOP protein, a BRAF protein, a p53 protein, a NCOA2 protein, a MAOA protein, a CAMK2N1 protein, COL3A1, CLDN8, HOXC6, TMEFF2, NPY, HPGD, BICD1, OR51E1 (PSGR), OR51E2 (PSGR2), NEFH, MSMB, CACNA1D, PLA2G7, MYO6, CRISP3, TWIST1, JAG1, PCGEM1, PMEPA1, LTF, and ETV1 or ETV4.

8. The method of claim 7, wherein the at least one antibody binds to an ERG epitope formed by amino acids 42-66 of SEQ ID NO:1.

9. The method of claim 7, wherein the at least one antibody comprises an antibody that binds to a human ERG3 protein, an antibody that binds to a human AMACR protein, and an antibody that binds to a human PSA protein or a human NKX3.1 protein.

10. The method of claim 6, wherein the at least one nucleic acid probe detects expression of one of the following human genes: the Ets Related Gene (ERG), alpha-methylacyl-CoA racemase (AMACR), prostate specific antigen (PSA), nucleolin gene, phosphatase and tensin homolog (PTEN), Akt, c-Myc, RAF, p63, prostate specific membrane antigen (PSMA), NKX3.1, a human gene encoding a high molecular weight cytokeratin, SPARC, SPINK1, SPOP, BRAF, p53, NCOA2, MAOA, CAMK2N1, COL3A1, CLDN8, HOXC6, TMEFF2, NPY, HPGD, BICD1, OR51E1 (PSGR), OR51E2 (PSGR2), NEFH, MSMB, CACNA1D, PLA2G7, MYO6, CRISP3, TWIST1, JAG1, PCGEM1, PMEPA1, LTF, and ETV 1 or ETV4.

11. The method of claim 1, wherein the method is capable of detecting a prostate cancer cell in a biological fluid containing not more than 10 prostate cancer cells.

12. The method of claim 1, wherein the method is capable of detecting at least about 70% of prostate cancer cells in a urine sample containing 100 prostate cancer cells.

13. The method of claim 1, wherein the method does not include a centrifugation step.

14. The method of claim 1, wherein the reagent for fixing cells is Saccomanno's fixative.

15. The method of claim 1, wherein the at least one detectable reagent comprises at least one antibody and wherein the at least one antibody comprises an antibody that binds a human Ets Related Gene protein.

16. The method of claim 1, wherein the urine contains not more than 100 prostate cancer cells.

17. The method of claim 1, wherein the urine is obtained from a subject after a digital rectal examination.

* * * * *